(12) United States Patent
Hwang et al.

(10) Patent No.: US 8,895,297 B2
(45) Date of Patent: *Nov. 25, 2014

(54) MICRO-DEVICE AND METHODS FOR DISRUPTING CELLS

(75) Inventors: Kyu-youn Hwang, Yongin-si (KR);
Joon-ho Kim, Yongin-si (KR);
Sung-hong Kwon, Yongin-si (KR);
Chin-sung Park, Yongin-si (KR);
Hee-kyun Lim, Yongin-si (KR); Sun-ok Jung, Hwaseong-si (KR); Won-jong Jung, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 22 days.

This patent is subject to a terminal disclaimer.

(21) Appl. No.: 13/492,179

(22) Filed: Jun. 8, 2012

(65) Prior Publication Data

US 2012/0309004 A1 Dec. 6, 2012

Related U.S. Application Data

(63) Continuation-in-part of application No. 13/275,871, filed on Oct. 18, 2011.

(30) Foreign Application Priority Data

Oct. 29, 2010 (KR) .................. 10-2010-0107014

(51) Int. Cl.

| C12N 1/06 | (2006.01) |
|---|---|
| C12M 1/00 | (2006.01) |
| B01L 3/00 | (2006.01) |
| C12M 1/33 | (2006.01) |
| C12M 3/08 | (2006.01) |
| C12M 3/00 | (2006.01) |

(52) U.S. Cl.
CPC ............... *C12M 47/06* (2013.01); *C12N 1/06* (2013.01); *B01L 3/502753* (2013.01); *B01L 2300/0816* (2013.01); *B01L 2300/0867* (2013.01); *B01L 2400/0481* (2013.01)
USPC ...................................... 435/306.1; 435/173.7

(58) Field of Classification Search
CPC ............ C12N 1/06; C12N 1/063; C12N 1/066
See application file for complete search history.

(56) References Cited

U.S. PATENT DOCUMENTS

| 2008/0014122 A1 | 1/2008 | Kim et al. |
| 2010/0167384 A1 | 7/2010 | Clemmens et al. |

FOREIGN PATENT DOCUMENTS

| CN | 101415813 A | 4/2009 |
| EP | 1 797 956 A1 | 6/2007 |
| WO | WO 03/015922 A1 | 2/2003 |
| WO | WO 03/015923 A1 | 2/2003 |
| WO | 2008/030631 A2 | 3/2008 |
| WO | WO 2008/104916 A2 | 9/2008 |

OTHER PUBLICATIONS

Hwang et al., Miniaturized bead-beating device to automate full DNA sample preparation processes for Gram-positive bacteria, *Lab Chip*, 2011, 11: 3649-3655.
Kido et al., "A novel, compact disk-like centrifugal microfluidics system for cell lysis and sample homogenization," *Collides and Surface B: Biointerfaces*, 2007, 58: 44-51.
Kim et al, "Cell lysis in a microfluidic CD (compact disk)," *Lab Chip*, 2004, 4: 516-522.
Lin et al., "Cell lysis methods for high-throughput screening or miniaturized assays," *Biotechnology Journal*, 2009, 4: 210-215.
Weibel et al., "Microfabrication meets microbiology," *Nature Reviews: Microbiology*, 2007, 5: 209-218.
Chinese Office Action in Application No. 2011-10332898.9, issued Jun. 24, 2014.
Zhanglin et al., "Cell Lysis methods for high-throughput screening or miniaturized assays", *Biotechnology Journal*, vol. 4, No. 2, pp. 210-215 (2009).

*Primary Examiner* — James Martinell
(74) *Attorney, Agent, or Firm* — Leydig, Voit & Mayer, Ltd.

(57) ABSTRACT

A micro-device for disrupting cells includes a first chamber in which the cells are disrupted, a second chamber which is pressurized and depressurized, a flexible membrane which separates the first chamber and the second chamber and is vibrated by pressuring and depressurizing the second chamber, and a micro-unit confined in the first chamber, where the micro-unit disrupts the cells in the first chamber.

11 Claims, 5 Drawing Sheets

MICRO-DEVICE AND METHODS FOR DISRUPTING CELLS

CROSS-REFERENCE TO RELATED APPLICATIONS

This application is a continuation-in-part of U.S. patent application Ser. No. 13/275,871, which claims priority to Korean Patent Application No. 10-2010-0107014, filed on Oct. 29, 2010, and all the benefits accruing therefrom under 35 U.S.C. §119, the content of which in its entirety is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 588 Byte ASCII (Text) file named "710372SequenceListing.txt," created on Jun. 8, 2012.

BACKGROUND

1. Field

The present disclosure relates to a device for separating and/or disrupting cells, and more particularly, to a micro-device for separating and/or disrupting cells and a method for disrupting cells using the micro-device.

2. Description of the Related Art

A nucleic acid-based micro total analysis system ("μTAS") is a promising platform for analyzing molecules. In such an analytic system, all analysis processes, e.g., a nucleic acid sample preparation process, an amplification process and a detection process, are integrated on a microchip and are automated. Real-time polymerase chain reaction ("PCR") process has been widely used since additional post-PCR analysis processes, e.g., electrophoresis and fluorescent imaging, may be omitted, thereby saving time and reducing complexity.

However, the sample preparation process for obtaining a nucleic acid suitable for PCR from a raw sample has not been effectively integrated into the entire analysis process on a microchip. Impurities in a sample may directly affect the specificity and sensitivity of PCR. Accordingly, elimination of impurities in a sample may substantially improve the amplification process.

Moreover, a target analyte in a sample is concentrated from an initial large volume to a small volume, and thus the initial sample having a volume of milliliters (ml) may be processed in the micro-device. Such a property improves PCR sensitivity, and is of great merit in using the micro-device beyond the capacities of laboratory equipment. Accordingly, inclusion of such functions in the device for nucleic acid preparation may substantially improve the application of the microfluidic analysis system.

The nucleic acid preparation process typically includes cell disruption for releasing nucleic acid from inside a cell to outside the cell. Cell disruption may include a process for disrupting cell membranes or cell walls. In particular, gram positive bacteria have a very thick peptidoglycan layer. Accordingly, it is more difficult to disrupt the cell membranes of gram positive bacteria than those of gram negative bacteria. *Staphylococcus aureus* ("*S. aureus*"), *Streptococcus pneumoniae*, and *Enterococcus* species, are examples of gram positive bacteria. An example of a *Staphylococcus aureus* species is methicillin-resistant *Staphylococcus aureus* ("MRSA") and *Enterococcus* species include Vancomycin-resistant *Enterococcus* ("VRE"). *Streptococcus pneumoniae* is a causative pathogen of, for example, pneumonia and sepsis.

SUMMARY

Provided is a micro-device for separating and/or disrupting cells, which facilitates cell disruption.

Provided is a method for disrupting cells using the micro-device for disrupting cells.

Additional aspects will be set forth in part in the description which follows and, in part, will be apparent from the description, or may be learned by practice of the embodiments set forth herein.

According to an embodiment of the invention, a micro-device for separating and/or disrupting cells includes a first chamber in which the cells are disrupted, a second chamber which is pressurized and depressurized, a flexible membrane which separates the first chamber and the second chamber and is vibrated by pressuring and depressurizing the second chamber, and a micro-unit confined in the first chamber, where the micro-unit disrupts the cells in the first chamber.

In an embodiment, the micro-unit may include a plurality of solid supports. The solid support may be present as a separate material with respect to the first chamber wall, i.e., present in the inner space of the first chamber without permanently attached to the wall of the chamber. The solid support are not limited to microscale dimensions, and may have any dimensions so long as a cell can be separated and/or lysed by the operation of the cell lysis device. The solid support may be a microparticle. The term "microparticle" refers to a particle having the longest length in the cross-section of the solid support up to about 1000 μm. For example, the longest length may be from about 10 nanometers (nm) to about 1000 μm, specifically about 10 nm to about 700 μm, more specifically about 10 nm to about 500 μm, or about 10 nm to about 300 μm, or about 10 nm to about 100 μm, or about 10 nm to about 50 μm, or about 10 nm to about 10 μm in size, and in an embodiment, may be from about 50 nm to about 1000 μm, specifically about 50 nm to about 900 μm, more specifically about 50 nm to about 700 μm, or about 50 nm to about 500 μm, or about 50 nm to about 300 μm, or about 50 nm to about 100 μm, or about 50 nm to about 50 μm, or about 50 nm to about 10 μm in size, and in another embodiment, may be from about 100 nm to about 1000 μm, specifically about 100 nm to about 900 μm, more specifically about 100 nm to about 700 μm, or about 100 nm to about 500 μm, or about 100 nm to about 300 μm, or about 100 nm to about 100 μm, or about 100 nm to about 50 μm, or about 100 nm to about 10 μm, and in yet another embodiment, may be from about 1 μm to about 500 μm, specifically about 1 μm to about 300 μm, more specifically about 1 μm to about 100 μm, or about 1 μm to about 50 μm, or about 1 μm to about 30 μm, or about 1 μm to about 10 μm in size. The solid support may be at least one of spherical, planar, or multi-planar. The solid support may be microbeads. The solid supports in the first chamber may be at least one, for example two in number. In an embodiment, the number of solid supports in the first chamber may be 10 or greater, specifically 100 or greater, more specifically 1000 or greater, or 10,000 or greater, or 100,000 or greater, or $10^8$ or greater. For example, the number of solid supports in the first chamber may be from about 1 to about $10^8$, specifically about 100 to about $10^6$. The first chamber may be manufactured such that the solid supports are placed in a space and blocked by the first chamber, so that the solid supports, for example beads may be unable to pass out of an inlet or an outlet. A density D of the solid supports in the first chamber may be greater than or equal to 1 gram per cubic centimeter ($g/cm^3$), specifically about 1 g/cm³ to about 20 g/cm³, more specifically about 1 g/cm³ to about 15 g/cm³, or about 1 g/cm³ to about 10 g/cm³, or about 1 g/cm³ to about 8 g/cm³, or about 1 g/cm³ to about 6 g/cm³, or about 1 g/cm³ to about 4 g/cm³, or about 3 g/cm³ to about 20 g/cm³, or about 3 g/cm³ to about 15 g/cm³, or about 3 g/cm³ to about 10 g/cm³, or about 3 g/cm³ to about 8 g/cm³, or about 3 g/cm³ to about 6 g/cm³, or about 3 g/cm³ to about 4 g/cm³.

In an embodiment, the first chamber may include an inlet, through which the cells are introduced, and an outlet, through which contents of disrupted cells are released.

In an embodiment, the second chamber may include a plurality of sub-chambers.

In an embodiment, the solid support may be a plurality of microbeads and the plurality of microbeads may include at least one of a glass bead, a metallic bead and a metal oxide bead.

In an embodiment, the micro-unit may further include a binding material which binds to one or more cells or viruses on its surface. The binding material may an organic layer disposed on a surface of the plurality of solid support for example, microbeads.

In an embodiment, at least one of a wall of the first chamber and a surface of the solid supports such as microparticles may comprise a binding material which is able to bind to a cell or virus, and in an embodiment, may be coated with the binding material. The binding material may be a material which specifically binds to the cell or virus. The specific binding material may be at least one of an antibody for an antigen, a substrate or inhibitor for an enzyme, an enzyme for a substrate, a receptor for a ligand, and a ligand for a receptor. The binding material may be a material which non-specifically binds to the cell or virus. The nonspecific binding material may be a hydrophobic material having a water contact angle of about 70° to about 95°, and in an embodiment, may include a material with at least one amino group. The material with at least one amino group may include a polymer having at least two amino groups. The material with at least one amino group may include polyethyleneimine ("PEI"). The hydrophobic material with a water contact angle of about 70° to about 95° may include octadecyldimethyl(3-trimethoxysilyl propyl) ammonium ("OTC") or tridecafluorotetrahydrooctyl-trimethoxylsilane ("DFS"). The wall of the first chamber or the surface of the solid supports comprising the binding material may be of use in capturing or adsorbing the cell or virus to separate.

The material with at least one amino group may an aminosilane moiety having at least one amino group selected from primary amino group, secondary amino group, tertiary amino group, and quaternary amino group. The tertiary amino group may be any tertiary amino group, except that a amide group or a nitrile group may not be used when used alone. The aminosilane moiety may be derived from an aminosilane molecule by depositing the surface of the nonplanar solid support. The aminosilane molecule may be an organic aminosilane molecule having a formula $(X_1)(X_2)(X_3)Si(Y)$, wherein $X_1$, $X_2$ and $X_3$ are independently selected from the group consisting of hydrogen, alkoxy group (—OR) and halogen and at least one of $X_1$, $X_2$ and $X_3$ is alkoxy group. In the alkoxy group (—OR), R may be a hydrocarbonyl group having one to 20 carbon atoms, for example, methyl, ethyl, propyl, iso-propyl etc. The halogen may be F, Cl, Br, I or At. Y may an organic moiety containing at least one amino group. The organic moiety may be aminoalkyl, or polyethyleneimine. In the aminoalkyl, the alkyl group may have one to 20 carbons atoms. The polyethyleneimine may have the formula $-[CH_2CH_2NH]_n-$, wherein n may be 2-100. The alkoxy groups (—OR) hydrolyze in an aqueous environment, producing hydroxyl group, one or more of which may undergo condensation and elimination reactions with surface —OH groups found on the surface of the solid support as well as on neighboring organosilane molecules. The aminosilane molecule may 3-aminopropyltriethoxysilane (GAPS), polyethyleneiminetrimethoxysilane such as N-(2-aminoethyl)-3-aminopropyltriethoxysilane (EDA) and (3-trimethoxysilyl-propyl)diethylenetriamine (DETA). The aminosilane molecules may be coated on the surface of the solid support by a known method. For example, the coating may be conducted by using dip-coating method or chemical vapor deposition (CVD) method. The dip-coating method may be conducted according to following exemplary procedure: solid supports such as glass substrates may be cleaned using a general glass cleaning protocol: immersion in NaOH (2.5 M) solution for 24 h, sonication in $H_2O$ for 10 min, immersion in HCl (0.1 M) for 15 min, sonication in $H_2O$ for 10 min and immersion in methanol for 5 min prior to the silanization step. Silanization of the samples may be performed by dip coating in 1% aqueous solutions of silane for 15 min. Post-treatment steps may include shaking in methanol for 5 min, rinsing in $H_2O$ for 10 min and finally spin drying (2000 rpm) for 5 min. The coated slides may be baked at 110° C. for 15 min and stored in a vacuum desiccator prior to analysis. Further, the dip-coating method may be conducted according to the method described in the examples. The CVD method may be conducted according to following exemplary procedure: solid supports such as a silicon wafer or the glass substrates. Using a pulsed CVD technique (ThinSonic pulsed ultrasonic CVD; Sono-Tech Corp.), different aminosilane molecule film such as GAPS film thicknesses may be deposited on the solid supports such as a silicon wafer or glass substrates. The pulsed ultrasonic method may be a process in which the precursor is delivered to the ultrasonic nozzle through a series of automatically controlled solenoid valves. The experimental apparatus may be known in the art. The precursor may atomized at the tip of the nozzle and introduced into a low-pressure reaction chamber in a near-vapor-phase state (about 15 μm drop diameter). Nozzle power, volume of pulses and number of pulses may be varied to obtain the desired coating thicknesses. All of the solid supports such as a silicon wafer or the glass substrates may be first cleaned in $NH_4OH:H_2O_2:H_2O$ (1:1:5) solution before the silane deposition step. The substrates may be heated (120° C.) in situ for 15 min prior to the pulses injections. The coated solid support may be dried under N2 without any post-washing steps.

In this application, the term "water contact angle" refers to water contact angle measured by a Kruss Drop Shape Analysis System type DSA 10 Mk2. A droplet of 1.5 ul deionized water is automatically placed on the sample. The droplet was monitored every 0.2 seconds for a period of 10 seconds by a CCD-camera and analyzed by Drop Shape Analysis software (DSA version 1.7, Kruss). The complete profile of the droplet was fitted by the tangent method to a general conic section equation. The angles were determined both at the right and left side. An average value is calculated for each drop and a total of five drops per sample are measured. The average of the five drops is taken the contact angle.

In an embodiment, a diameter of each of the plurality of spherical solid supports may be in a range of about 1 micrometer to about 500 micrometers.

In an embodiment, a density of the plurality of solid supports such as microbeads may be in a range of about 1 gram per cubic centimeter to about 20 grams per cubic centimeter. In an embodiment, the solid supports such as beads may be rigid enough to be used as a cell lysis media. Solid supports, as used herein, refer to spherical bodies or non-spherical bodies, and can have any shape so long as the shape does not adversely affect the desirable features of the disclosed method or device. The solid supports may comprise a solid material at least a part thereof, and in an embodiment, may include a coating with a solid material. In an embodiment, the solid supports are a solid particle. In another embodiment, the beads are hollow. The beads may be magnetic or nonmagnetic. The beads may comprise at least one of a glass, metal, and metal oxide. In an embodiment, the beads comprise at least one of glass beads, metal beads, and metal oxide beads. The metal oxide may comprise at least one of $ZrO_2$, $SiO_2$, $Al_2O_3$, $Fe_2O_3$, and $TiO_2$. In an embodiment, the solid supports comprise a combination of, for example, $ZrO_2$ and $SiO_2$. The metal beads may comprise, for example, steel beads or stainless steel beads. Glass beads are specifically mentioned.

In an embodiment, a size of at least one of the inlet and the outlet may be less than a size of the micro-unit.

In an embodiment, a size of at least one of the inlet and the outlet may be greater than a size of the micro-unit, and the first chamber may further include at least one projection on an inner surface of the at least one of the inlet and the outlet, where the at least one projection makes an effective size of the at least one of the inlet and the outlet less than a size of the micro-unit.

In an embodiment, a thickness of the membrane may be in a range of about 1 micrometer to about 5 millimeters. The membrane may be flexible and elastic and thus, may be extended to upward or downward by pressuring and depressurizing the second chamber. The flexible and elastic membrane may be placed between the first chamber and the second chamber and define at least a part of the wall of the first chamber and second chamber so as to be able to be vibrated by pressuring and depressurizing the second chamber. The membrane may comprise an elastic polymer membrane, such as a polydimethylsiloxane ("PDMS") membrane.

In an embodiment, the cells may include at least one of bacteria, virus and fungi. According to another embodiment of the invention, a method of disrupting cells includes: introducing cells into a first chamber of a micro-device for disrupting cells, where the micro-device includes the first chamber, a second chamber which is pressurized and depressurized, a flexible membrane which separates the first chamber and the second chamber and is vibrated by pressurizing and depressurizing the second chamber, and a micro-unit for disrupting cells confined in the first chamber; disrupting the cells by vibrating the flexible membrane between the first chamber and the second chamber, after the introducing the cells; and releasing resultant disrupted cells from the first chamber of the micro-device.

In an embodiment, the introducing the cells may include passing a solution containing the cells through the first chamber.

In an embodiment, the method may further include providing a cell lysis solution to the first chamber.

In an embodiment, the disrupting of the cells may include vibrating the plurality of micro-units by vibrating the flexible membrane which separates the first chamber from the second chamber. The micro-units are as described herein above. The micro-units such as a solid support for disrupting cells are contained in the first chamber and may be present as a separate material with respect to the chamber wall, i.e., present in the inner space of the first chamber without permanently attached to the wall of the chamber.

In an embodiment, the cell lysis solution may include at least one of NaOH, KOH, chaotrope, a surfactant, cell wall degrading enzyme and a biological buffer.

In an embodiment, the disrupting the cells may include periodically or non-periodically adjusting the pressure of the interior of the second chamber such that the flexible membrane is vibrated.

In an embodiment, the disrupting the cells may include vibrating the flexible membrane at a range of about 0.001 hertz to about 100 kilohertz.

In an embodiment, the method may further include disrupting the cells by vibrating the flexible membrane between the first chamber and the second chamber, after the introduction of the cells. The membrane may be flexible and elastic and thus, may be extended to upward or downward by pressuring and depressurizing the second chamber. The flexible and elastic membrane may be placed between the first chamber and the second chamber and define at least a part of the wall of the first chamber and second chamber so as to be able to be vibrated by pressuring and depressurizing the second chamber.

In an embodiment, the micro-unit may include a micro-bead.

In an embodiment, the step of introducing the cells or viruses may comprise passing a solution containing the cells or viruses at a rate of 100 to 500 ul/min through the first chamber such that the cells or viruses in the solution is retained on the solid support and the first chamber has a volume of 1 ul to 100 ul and the solution has a pH of 3.0 to 6.0 and a salt concentration of 10 mM to 500 mM, wherein the solid support comprises a binding material which binds to a cell or a virus on its surface.

The binding material may be a material which specifically binds to the cell or virus. The specific binding material may be at least one of an antibody for an antigen, a substrate or inhibitor for an enzyme, an enzyme for a substrate, a receptor for a ligand, and a ligand for a receptor. The binding material may be a material which non-specifically binds to the cell or virus. The nonspecific binding material may be a hydrophobic material having a water contact angle of about 70° to about 95°, and in an embodiment, may include a material with at least one amino group. The material with at least one amino group may include a polymer having at least two amino groups. The material with at least one amino group may include polyethyleneimine ("PEI"). The hydrophobic material with a water contact angle of about 70° to about 95° may include octadecyldimethyl(3-trimethoxysilyl propyl)ammonium ("OTC") or tridecafluorotetrahydrooctyl-trimethoxylsilane ("DFS"). The wall of the first chamber or the surface of the solid supports comprising the binding material may be of use in capturing or adsorbing the cell or virus to separate.

The material with at least one amino group may an aminosilane moiety having at least one amino group selected from primary amino group, secondary amino group, tertiary amino group, and quaternary amino group. The tertiary amino group may be any tertiary amino group, except that a amide group or nitrile group may not be used when used alone. The aminosilane moiety may be derived from an aminosilane molecule by depositing the surface of the nonplanar solid support. The aminosilane molecule may be an organic aminosilane molecule having a formula $(X_1)(X_2)(X_3)Si(Y)$, wherein $X_1$, $X_2$ and $X_3$ are independently selected from the group consisting of hydrogen, alkoxy group (—OR) and halogen and at least one of $X_1$, $X_2$ and $X_3$ is alkoxy group. In the alkoxy group (—OR), R may be a hydrocarbonyl group having one to 20 carbon atoms, for example, methyl, ethyl, propyl, iso-propyl etc. The halogen may be F, Cl, Br, I or At. Y may an organic moiety containing at least one amino group. The organic moiety may be aminoalkyl, or polyethyleneimine. In the aminoalkyl, the alkyl group may have one to 20 carbons atoms. The polyethyleneimine may have the formula —[$CH_2CH_2NH$]$_n$—, wherein n may be 2-100. The alkoxy groups (—OR) hydrolyze in an aqueous environment, producing hydroxyl group, one or more of which may undergo condensation and elimination reactions with surface —OH groups found on the surface of the solid support as well as on neighboring organosilane molecules. The aminosilane molecule may be 3-aminopropyltriethoxysilane (GAPS), polyethyleneiminetrimethoxysilane such as N-(2-aminoethyl)-3-aminopropyltriethoxysilane (EDA) and (3-trimethoxysilylpropyl)diethylenetriamine (DETA). The aminosilane molecules may be coated on the surface of the solid support by a known method. For example, the coating may be conducted by using dip-coating method or chemical vapor deposition (CVD) method. The dip-coating method may be conducted according to following exemplary procedure: solid supports such as glass substrates may be cleaned using a general glass cleaning protocol: immersion in NaOH (2.5 M) solution for 24 hours, sonication in H2O for 10 min, immersion in HCl (0.1 M) for 15 min, sonication in H2O for 10 min and immersion in methanol for 5 min prior to the silanization step. Silanization of the samples may be performed by dip coating in 1% aqueous solutions of silane for 15 min. Post-treatment steps may include shaking in methanol for 5 min, rinsing in H2O for 10 min and finally spin drying (2000 rpm) for 5 min. The coated slides may be baked at 110° C. for 15 min and stored in a vacuum desiccator prior to analysis. The CVD method may be conducted according to following exemplary procedure: solid supports such as a silicon wafer or the glass substrates. Using a pulsed CVD technique (Thin-Sonic pulsed ultrasonic CVD; Sono-Tech Corp.), different aminosilane molecule film such as GAPS film thicknesses may be deposited on the solid supports such as a silicon wafer or glass substrates. The pulsed ultrasonic method may be a process in which the precursor is delivered to the ultrasonic nozzle through a series of automatically controlled solenoid valves. The experimental apparatus may be known in the art. The precursor may atomized at the tip of the nozzle and introduced into a low-pressure reaction chamber in a near-vapor-phase state (about 15 μm drop diameter). Nozzle power, volume of pulses and number of pulses may be varied to obtain the desired coating thicknesses. All of the solid supports such as a silicon wafer or the glass substrates may be first cleaned in NH4OH:H2O2:H2O (1:1:5) solution before the silane deposition step. The substrates may be heated (120° C.) in situ for 15 min prior to the pulses injections. The coated solid support may be dried under N2 without any post-washing steps. In this application, the term "water contact angle" refers to water contact angle measured by a Kruss Drop Shape Analysis System type DSA 10 Mk2. A droplet of 1.5 mu.l deionized water is automatically placed on the sample. The droplet was monitored every 0.2 seconds for a period of 10 seconds by a CCD-camera and analyzed by Drop Shape Analysis software (DSA version 1.7, Kruss). The complete profile of the droplet was fitted by the tangent method to a general conic section equation. The angles were determined both at the right and left side. An average value is calculated for each drop and a total of five drops per sample are measured. The average of the five drops is taken the contact angle. In an embodiment of the invention, the method may further comprise washing the solid support with wash buffer by flowing the wash buffer at a rate of 100 to 500 ul/min through the first chamber to remove impurities form the solid support, wherein the wash buffer has a pH of 3.0 to 9.0, for example 3.0 to 6.0, 3.0 to 7.0 or 3.0 to 8.0, and a salt concentration of 10 mM to 500 mM. The wash buffer may be acetate buffer or phosphate buffer or TRIS buffer. The solution comprising cells or viruses comprises both animal cells and bacterial cells, and the impurities are animal cells, thereby after the step of washing, the animal cells are selectively removed from the solid support and retaining bacterial cells to the solid support.

In an embodiment of the invention, prior to the step of introducing, the method may further include diluting a sample comprising cells or viruses with a phosphate buffer or an acetate buffer having a pH of 3.0 to 6.0 and salt concentration of 10 mM to 500 mM to obtain a solution containing cells or viruses having a pH of 3.0 to 6.0 and salt concentration of 10 mM to 500 mM.

In an embodiment, the method further includes performing polymerase chain reaction (PCR) using the lysed product obtained from the disrupting step as a template without any further purification step. The sample containing the cells or viruses may be blood or a sample containing the blood derived material such red blood cell, white blood cells, platelets etc. Thus, PCR amplification may be achieved with rapidity and convenience since no further step for removing the PCR inhibitor is required. The lysis solution may be NaOH for example, 0.0001 N to 0.1 N NaOH.

According to another embodiment of the invention, a micro-device includes a membrane, a first chamber which is partly delimited by the membrane, a second in the first chamber, where the plurality of microparticles contacts the membrane, and a port in fluid communication with the second chamber, where the membrane is vibrated by pressurizing and depressurizing the second chamber.

In an embodiment, a density of the plurality of microparticles may be in a range of about 1 gram per cubic centimeter to about 20 grams per cubic centimeter.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, embodiments of the invention will be described in further detail with reference to the accompanying drawings.

Figure 1:
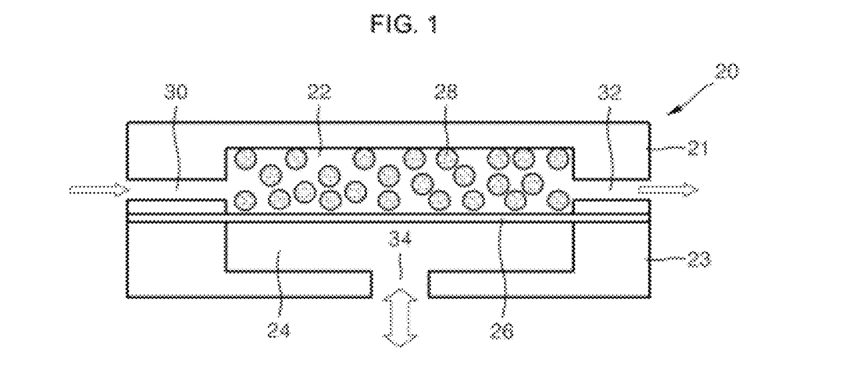
FIG. 1 is a cross sectional view of an embodiment of a micro-device for disrupting cells in a molecular diagnostic apparatus according to the invention.
Figure 2:
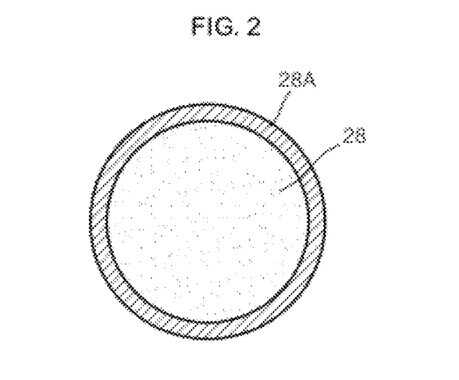
FIG. 2 is a cross section view of an embodiment of a bead including an organic layer thereon.

FIG. 1 is a cross sectional view of an embodiment of a micro-device for disrupting cells in a molecular diagnostic apparatus, and FIG. 2 is a cross section view of an embodiment of a bead including an organic layer thereon.

Referring to FIG. 1, the micro-device 20 includes an upper plate 21, a lower plate 23 and a membrane 26. The membrane 26 is disposed between the upper plate 21 and the lower plate 23. A space in a portion of the upper plate 21 defines a first chamber 22, and a space in a portion of the lower plate 23 defines a second chamber 24. The first chamber 22 and the second chamber 24 are separated by the membrane 26, disposed between the first chamber 22 and the second chamber 24. In such an embodiment, the first chamber 22 is delimited by the upper plate 21 and the membrane 26, and the second chamber 24 is delimited by the lower plate 23 and the membrane 26. In some embodiments, each of the first chamber and the second chamber may have a volume in a range from about 1 microliter (ul) to about 10,000 microliters (ul).

The membrane 26 may be flexible. In an embodiment, the membrane 26 may be a polymer membrane, such as polydimethylsiloxane ("PDMS") membrane, for example. The thickness of the membrane 26 may be, for example, in a range from about 1 micrometer (um) to about 5 millimeters (mm). The membrane 26 may be liquid and gas-permeable, but it may also be partly permeable.

The first chamber 22 may include a plurality of microunits, e.g., a plurality of particles. The micro-units may be magnetic or non-magnetic micro-units. In an embodiment, the particles may be a plurality of beads 28, as shown in FIG. 1. Since the first chamber 22 is delimited by the membrane 26, the beads 28 may contact with the membrane 26. In an embodiment, the beads 28 may be microbeads. In the exemplary embodiment shown in FIG. 1, the micro-units include the plurality of beads 28, but the invention is not limited thereto. In an alternative embodiment, other units may be included in the first chamber 22 instead of the plurality of beads 28. In an embodiment, the diameter of each bead 28 may be, for example, in the range of about 1 um to about 500 um. The density of beads 28 in the first chamber 22 may be greater than about 1 gram per cubic centimeter ($g/cm^3$), for example, in the range of about 1 $g/cm^3$ to about 20 $g/cm^3$. In an embodiment, at least one bead may be included in the liquid medium, for example, there may be 10, 100, 1000, 10,000, $10^5$, $10^6$, $10^7$, $10^8$, or $10^9$ or more beads per 1 microliter (ul) of the liquid medium. In some embodiments, 1 to $10^8$ beads, for example, 100 to $10^6$ beads, may be included per 1 ul of the liquid medium in the first chamber 22. The microunits may have a sphere shape, a plate shape, or may have a shape including a plurality of sides. The micro-units may be magnetic or non-magnetic beads. In an embodiment, the beads 28 may be glass beads. In an alternative embodiment, the beads 28 may be metal oxide beads or metallic beads.

The metal oxide may be one of $ZrO_2$, $SiO_2$, $Al_2O_3$, $Fe_2O_3$, $TiO_2$ and a mixture thereof. In one embodiment, the mixture may be, for example, a mixture including $ZrO_2$ and $SiO_2$. The metal beads may be, for example, formed of steel or stainless steel. In an embodiment, the beads 28 have a composition of glass or metal oxide, and surface modifications for cell capture or absorption are thereby effectively implemented.

In an embodiment, surfaces of the beads 28 may be capable of binding to a cell or may be modified to be suitable for cell capture by binding to a cell. The surfaces of the beads 28 may be hydrophobic, for example, have a water contact angle in a range of 70° to 95°. The hydrophobicity may be rendered, for example, by coating the surfaces of the beads 28 with compounds such as octadecyldimethyl(3-trimethoxysilylpropyl) ammonium ("OTC") or tridecafluoro tetrahydrooctyltrimethoxysilane ("DFS"). The surfaces of the beads 28 may also be coated with polyethyleneimine trimethoxy silane ("PEIM"). The surfaces of the beads 28 may have cell-binding substances immobilized thereon, such as an antibody which binds to an antigen on a cell surface, a receptor which binds to a ligand on a cell surface, or a ligand which binds to a receptor on a cell surface, for example. In an embodiment, the surfaces of the beads 28 include substances capable of specifically binding to specific cells such that the beads 28 specifically separate specific cells. In an alternative embodiment, the surfaces of the beads 28 include substances capable of non-specifically binding to cells such that the beads 28 non-specifically separate all kinds of cells.

The cells may include bacteria, a virus or fungi. The cells may be contained in an appropriate liquid medium. The liquid medium may be, for example, a medium for cell culture, a buffer, for example, phosphate buffered saline ("PBS"), physiological saline, body fluids or water. The liquid medium may also include a cell lysis solution. The cell lysis solution may be additionally and separately supplied to the chamber after the liquid medium containing the cells is supplied, or may be pre-mixed and then supplied to the chamber. The cell lysis solution may include a non-specific cell lysis agent and/or a specific cell lysis agent. The non-specific cell lysis agent may include at least one of a surfactant, NaOH and a chaotropic salt. The specific cell lysis agent may include, cell wall degrading enzyme for example, lysozyme, lysostaphin or penicillin and beta-lactam antibiotics.

The cells bound to the micro-units may be washed, after the cells are introduced into the first chamber 22. The washing may be carried out by passing a wash solution through the first chamber 22 with or without the liquid medium. The wash solution may wash off unbound substances, leaving the cells bound to the micro-units. The wash solutions may be, for example, water, a buffer (such as a PBS buffer) or physiological saline.

In one embodiment, the cells may be disrupted while the cells are introduced into the first chamber 22. In an alternative embodiment, the cells may be disrupted after the cells are introduced into the first chamber 22.

The micro-device 20 includes an inlet 30 and an outlet 32. The sizes of the inlet 30 and outlet 32 may be smaller than a size of the micro-units, e.g., a diameter of each bead 28. In one exemplary embodiment, the inlet 30 and the outlet 32 may have a circular cross-sectional shape, and the diameters of the inlet 30 and the outlet 32 may be less than the diameter of the bead 28. A solution containing cells to be disrupted is introduced into the first chamber 22 through the inlet 30. Resultant disrupted cells, including a nucleic acid, for example, obtained by the disruption of cell membrane and/or walls are released through the outlet 32. The inlet 30 may be formed through one wall of the upper plate 21 to connect to one side of the first chamber 22. The outlet 32 may be formed through another wall of the upper plate 21 to connect to the other side of the first chamber 22.

In an embodiment, at least one of the inlet 30 and outlet 32 may be operatively connected to a unit for providing power (not shown). The unit for providing power can provide a power to move a fluid through at least one of the inlet 30 and outlet 32. The unit for providing power may include a unit causing the motion of fluid, for example, a unit that provides a positive pressure or a negative pressure to the first chamber 22, including a pump. The pump may be a micropump, which may be applied to a microfluidic device. The micropump may be a mechanical or a non-mechanical device. The mechanical micropump may include an actuator and moving parts which are membranes or flaps. The motion of fluid may be generated using a piezoelectric, electrostatic, thermo-pneumatic, pneumatic or magnetic effect. A non-mechanical device may function as the unit for providing the power by generating an electro-hydrodynamic force, or an electro-osmotic or ultrasonic flow.

The inlet 30 and the outlet 32 may be in fluid-communication with the first chamber 22, for example, through a microchannel (not shown). The microchannel may have a width in a range of about 1 um to about 10,000 um, for example about 1 um to about 5,000 um.

The first chamber 22 including the micro-units may be in fluid-communication with at least one of a storage unit (not shown) that stores a cell lysis solution and a storage unit (not shown) that stores cell wash solution. The storage units may be connected to the chamber through the inlet 30. The cells may be introduced by applying a positive pressure to an inlet 30 of the first chamber 22 or applying a negative pressure to the outlet 32 of the first chamber 22. In an embodiment, the negative pressure or positive pressure may be applied by a pump (not shown). The pump may be at least one of a peristaltic pump and a pneumatic pump. In an alternative embodiment, the cells may be introduced through direct infusion by a user. In one embodiment, for example, the cells may be infused by the user performing pipetting. The amount and rate of introduction may depend on the cells to be disrupted, the purpose of cell disruption, and the post-cell disruption process, for example, and one of ordinary skill in the art may appropriately adjust them. The application of the pressure may be carried out in a state in which both the inlet 30 and the outlet 32 are closed. That is, the cells may be disrupted in a closed chamber containing the cells. The application of the pressure may be also carried out in a state in which at least one of the inlet 30 and the outlet 32 is open. That is, the cells may be disrupted under conditions that at least a portion of the liquid medium containing the cells in the chamber is flowing.

The second chamber 24 may operate as a pneumatic chamber including a space into which a fluid, such as air, for pressing periodically or non-periodically on the membrane 26 is introduced. High-pressurized fluid is introduced into the second chamber 24, and thus the membrane 26 is pressed. When the membrane 26 is pressed, the membrane 26 protrudes toward the first chamber 22, and the spatial volume of the first chamber 22 is thereby reduced. When the membrane 26 is de-pressed, the membrane 26 shrinks down toward the second chamber 24. The second chamber 24 has a port 34 which is an inflow passage of the fluid that pressurizes the interior of the second chamber 24 and simultaneously is an outflow passage of the fluid. In an embodiment, the fluid may be periodically or non-periodically introduced into/the second chamber 24 through the port 34 or released from the second chamber 24 through the port 34, and thus the membrane 26 may be periodically or non-periodically vibrated. The vibration of the membrane 26 leads to a periodic or non-periodic pressure to the beads 28 in the first chamber 22 through direct contact with the beads 28 or through the solution contained in the first chamber 22. In such an embodiment, motion of the beads 28 is induced, and the beads 28 collide with each other or collide with an inner wall of the first chamber 22. Due to the motion of the beads 28, the cells introduced into the interior of the first chamber 22 are disrupted by being sheared or grinded, that is the cells may be disrupted by a shearing force or an impact force applied to the cell or by heat, which are induced by the motion of the micro-units. The pressurizing or depressurizing of the interior of the second chamber 24 through the introduction of the fluid into the second chamber 24 (applying a positive pressure) or release of the fluid from the second chamber 24 (applying a negative pressure) is effectively controlled with a vibration frequency in a range of from about 0.001 hertz (Hz) to about 100 kilohertz (kHz).

Referring to FIG. 2, surfaces of the beads 28 may have an organic layer 28A which allows for specific or non specific cell capture. In one embodiment, for example, an antibody or an aptamer, may be coated on the surfaces of the beads 28 to selectively capture a specific cell. In an embodiment, a nonspecific cell may be captured by a hydrophobic or electrostatic force.

The organic layer 28A may be formed by modifying the surfaces of beads 28 in various ways using organosilane.

In one embodiment, a portion having an affinity with a specific or nonspecific cell is on a surface of the beads 28, and the cells introduced into the first chamber 22 are captured by the portion on the surface of the beads 28. In such an embodiment, the vibration of the membrane 26 causes the motion of the beads 28, which makes beads collide with each other or with the inner surface of the wall of the first chamber 22, and the cells on the surface of the beads 28 may be disrupted by the collisions.

In an alternative embodiment, after supplying a solution containing the cells to be disrupted, a substance for increasing the cell disruption effect may be supplied in the first chamber 22, and then the cell disruption may be carried out. In an embodiment, the cell lysis solution may include the substance for increasing the cell disruption effect. The cell lysis solution may include, for example, NaOH, KOH, a chaotropic solution or a surfactant. In an embedment, the cell lysis solution may include a biological buffer such as Tris, phosphate, citrate, acetate and carbonate, for example, which does not increase the cell disruption effect. The cell lysis solution may be used in a concentration not affecting the post-cell disruption processes such as polymerase chain reaction ("PCR"), and thus PCR may be conducted after cell disruption without a further purification process. In such an embodiment, the substance is used in a concentration affecting PCR, and then a purification process is carried out. The cell lysis solution may be supplied after the cell disruption process, thereby facilitating the release of a nucleic acid.

In an alternative embodiment, a solution containing the cells may be supplied to the first chamber 22 and then the cell disruption may be carried out without additional supply of the cell lysis solution into the chamber 22.

FIGS. 3 to 6 are cross sectional views of alternative embodiments of the micro-device for disrupting cells in a molecular diagnostic apparatus according to the invention.

Figure 3:
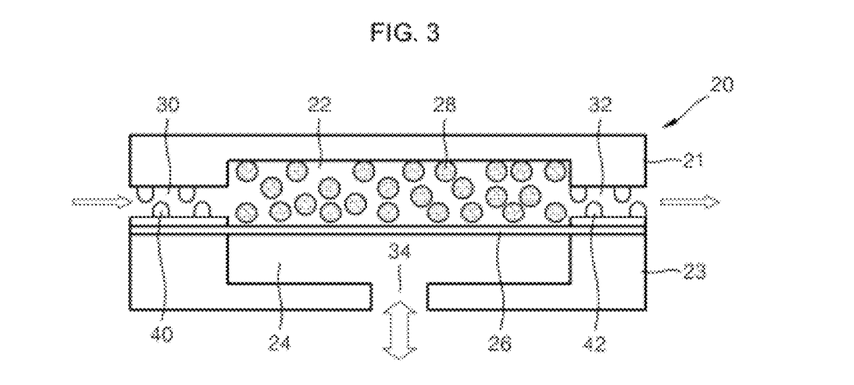
FIGS. 3 to 6 are cross sectional views of alternative embodiments of the micro-device for disrupting cells in a molecular diagnostic apparatus according to the invention.

FIG. 3 shows an alternative embodiment of the micro-device 20 of FIG. 1. The micro-device in FIG. 3 is substantially the same as the micro-device shown in FIG. 1 except for the inlet 30 and the outlet 32. The same or like elements shown in FIG. 3 have been labeled with the same reference characters as used above to describe the embodiment of the micro-device shown in FIG. 1, and any repetitive detailed description thereof will hereinafter be omitted or simplified.

Referring to FIG. 3, the sizes of the inlet 30 and the outlet 32 may be larger than a size of the bead 28. In one exemplary embodiment, the inlet 30 and the outlet 32 may have a circular cross-sectional shape, and the diameters of the inlet 30 and the outlet 32 may be greater than the diameter of the bead 28. A plurality of first projections 40 is disposed on an inner side of the inlet 30. The first projections 40 may be evenly distributed throughout the inner side of the inlet 30. The first projections 40 may be disposed in opposite direction with each other. Due to the first projections 40, the substantial size or effective size of the inlet 30, e.g., a size of a cross-sectional shape of the inlet 30 becomes smaller than the size of the beads 28. Similarly, a plurality of second projections 42 is disposed the inner side of the outlet 32. The distribution of the second projections 42 may be substantially the same as the distribution of the first projections 40. Due to the second projections 42, the substantial size or effective size of the outlet 32, e.g., a size of a cross-sectional shape of the outlet 32, may be smaller than the size of each bead 28. In an embodiment, the shapes of the first and second projections 40 and 42 may be substantially identical to each other. In an alternative embodiment, the shapes of the first and second projections 40 and 42 may be substantially different from each other. In an embodiment, the first and second projections 40 and 42 may be formed by embossing the inner sides of the inlet 30 and the outlet 32.

Figure 4:
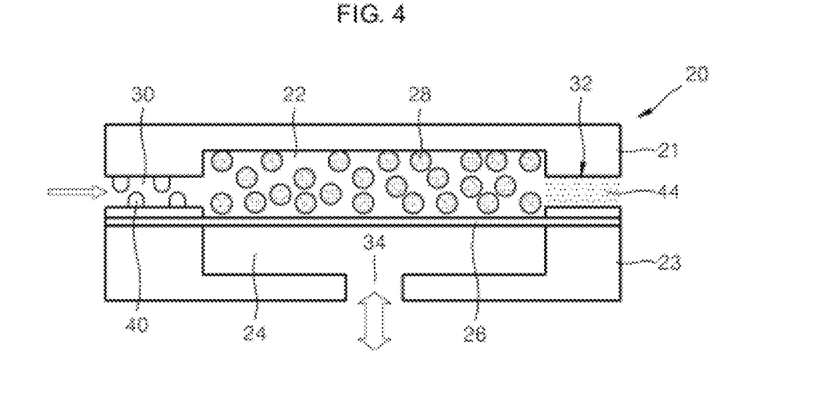

FIG. 4 shows another alternative embodiment of the micro-device 20 of FIG. 1. The micro-device in FIG. 4 is substantially the same as the micro-device shown in FIG. 1 except for the inlet 30 and the outlet 32. The same or like elements shown in FIG. 4 have been labeled with the same reference characters as used above to describe the embodiment of the micro-device shown in FIG. 1, and any repetitive detailed description thereof will hereinafter be omitted or simplified.

Referring to FIG. 4, the inlet 30 may be substantially the same as the inlet 30 of the embodiment shown in FIG. 3. In an embodiment, a filter 44 may be disposed in the outlet 32. The filter 44 may be a porous material which allows contents of the disrupted cells to pass. The size of the inlet 30 may be smaller than the size of the micro-unit, e.g., the size of each bead 28, as in FIG. 1.

Figure 5:
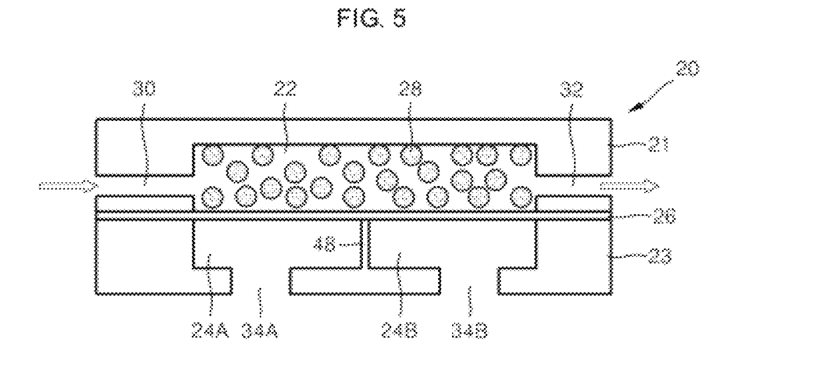

FIG. 5 shows another alternative embodiment of the micro-device 20 of FIG. 1. The micro-device in FIG. 5 is substantially the same as the micro-device shown in FIG. 1 except for the second chamber 24. The same or like elements shown in FIG. 5 have been labeled with the same reference characters as used above to describe the embodiment of the micro-device shown in FIG. 1, and any repetitive detailed description thereof will hereinafter be omitted or simplified Referring to FIG. 5, the second chamber 24 includes two chambers, e.g., a first sub-chamber 24A and a second sub-chamber 24B. The first sub-chamber 24A and the second sub-chamber 24B are separated by a partition wall 48. The role of the third and second sub-chambers 24A and 24B may be the same as that of the second chamber 24. The first sub-chamber 24A includes a first port 34A, and the second sub-chamber 24B includes a second port 34B. The structure of the first port and second port 34A, 34B may be substantially the same as the structure of the port 34 in the second chamber 24 of the embodiment shown in FIG. 1. The structural of the inlet 30 and the outlet 32 may be substantially the same as to the inlet and the outlet 32 of the embodiments shown in FIG. 3 or FIG. 4. The pressure may be applied to the first and second ports 34A and 34B, simultaneously or sequentially such that the membrane 26 of each sub-chamber vibrates simultaneously or sequentially. In an embodiment, the pressure may be applied with a same phase of pressure or different phases of pressure to the first and second ports 34A and 34B such that the first and second sub-chambers 24A and 24B vibrate in the same phase or different phases. In one embodiment, for example, the positive pressure is applied to the first port 34A and the negative pressure is applied to the second port 34B, and the membrane 26 of the first sub-chamber 24A and the membrane 26 of the second sub-chamber 24B thereby vibrate in opposite phases.

Figure 6:
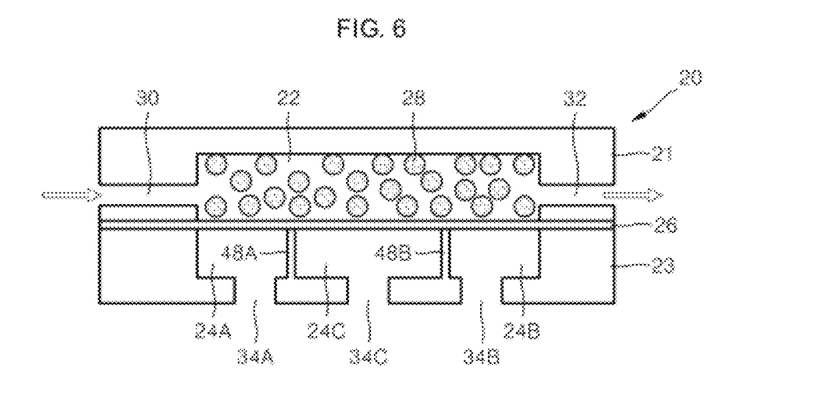

FIG. 6 shows another alternative embodiment of the micro-device 20. The micro-device in FIG. 6 is substantially the same as the micro-device shown in FIG. 1 except for the second chamber 24. The same or like elements shown in FIG. 6 have been labeled with the same reference characters as used above to describe the embodiment of the micro-device shown in FIG. 1, and any repetitive detailed description thereof will hereinafter be omitted or simplified Referring to FIG. 6, the second chamber 24 includes three sub-chambers, i.e., first to third sub-chambers 24A, 24B and 24C. The first to third sub-chambers 24A, 24B and 24C may perform a function substantially the same as the function that the second chamber 24 in FIG. 1 performs. The first sub-chamber and the third sub-chamber 24A and 24C are separated by a first partition wall 48A. The second sub-chamber and the third sub-chamber 24B and 24C are separated by a second partition wall 48B. The first to third sub-chambers 24A, 24B and 24C include first to third ports 34A, 34B and 34C, respectively. The structure and function of the first to third ports 34A 34B, and 34C may be substantially the same as the structure and function of the port 34 in FIG. 1. The second chamber 24 of the embodiment in FIG. 6 includes three sub-chambers, but the invention is not limited thereto. In an alternative embodiment, the second chamber 24 may include more than three sub-chambers. The pressure may be applied to the first to third ports 34A, 34B and 34C simultaneously or sequentially, allowing the membrane 26 in each chamber to vibrate simultaneously or sequentially. Also, a pressure may be applied at a same or different phase of pressure to the first to third ports 34A, 34B and 34C, enabling the membrane 26 of each chamber to vibrate in the same or different phase. In one embodiment, for example, the positive pressure may be applied to the first port 34A and the third port 34C, and the negative pressure may be applied to the second port 34B, such that the membrane 26 in the first sub-chamber and the third sub-chamber 24A and 24C and the membrane 26 in the second sub-chamber 24B vibrate in opposite phases to one another.

In the embodiments shown in FIGS. 1 and 3 to 6, the first chamber 22 is disposed above the second chamber 24, e.g., the first chamber 22 is an upper chamber and the second chamber 24 is a lower chamber, the invention is not limited thereto. In an alternative embodiment, the second chamber 24 may be disposed above the first chamber 22, e.g., the second chamber 24 may be the upper chamber and the first chamber 22 may be the lower chamber. The operations of the micro-device where the second chamber 24 is disposed above the first chamber 22 is substantially the same as the embodiments shown in FIGS. 1 and 3 to 6 where the first chamber 22 is disposed above the second chamber 24.

Hereinafter, the invention will be described with reference to the following examples. It should be understood that the exemplary embodiments described herein should be considered in a descriptive sense only and not for purposes of limitation.

EXAMPLE

1. Manufacture of a Micro-Device

A micro-device having three layers (e.g., glass layer-PDMS layer-glass layer) was manufactured. A channel and a chamber were formed on the glass wafer through conventional photographic and etching processes and a wet etching process.

After cleaning a 6 inch glass wafer (borosilicate glass, 700 um thickness) in a Piranha solution, e.g., a mixture of sulfuric acid ($H_2SO_4$) and hydrogen peroxide ($H_2O_2$), an amorphous polysilicon layer was vapor-deposited on the cleaned glass wafer to a thickness of 2000 um. Then, a patterning process was implemented, in which a part of the vapor-deposited polysilicon layer is exposed using a photoresist film. Then, the exposed part of the polysilicon layer was removed by dry etching. Thereafter, the photoresist film was stripped, and the exposed glass wafer was wet etched with a hydrofluoric acid solution (HF, 49%) to form a channel having a depth of 100 um and a width of 100 um. In the etching process to form the channel, a weir (projection) in a length of about 20 um was formed for isolating a bead. Next, the polysilicon layer was removed, and a dry film resist was coated and patterned. Then, a chamber (ca. 15.5 uL) for enclosing beads and holes were formed using a sand-blasting method. Thereafter, the glass wafer was diced into chip-shaped pieces, and cleaned with plasma. Then, a fluidic chip including the above-manufactured chamber in which beads are to be enclosed and a pneumatic chip including a chamber not enclosing the beads but functioning as a pneumatic pump were coupled to each other by way of a PDMS membrane (250 um thick) as an intermediate layer. FIG. 3. shows the micro-device manufactured in the present example.

About 15 mg to about 16 mg (about $2 \times 10^5$ in number) surface-modified glass beads were put into the produced bead chamber, the chamber was sealed using a tape, and the tape was covered with a plastic substrate to prevent the bending thereof upon operation. The surface-modified glass beads may be directly put into the bead chamber.

Pressurizing and depressurizing the pneumatic chamber for vibrating the PDMS membrane and the motion of solution were controlled by a solenoid valve, an electro-regulator and LabVIEW software.

2. Modification of a Glass Bead

After cleaning a glass bead (diameter: about 30 um to about 50 um, Polysciences, Inc.) in a Piranha solution, e.g., a mixture of sulfuric acid ($H_2SO_4$) and hydrogen peroxide ($H_2O_2$), the glass bead was sufficiently washed with distilled water and filtered under vacuum until dry. The glass bead may be spherical.

Next, the bead was put into ethanol having 5 volume percent (% v/v) trimethoxysilylpropyl-modified (polyethyleneimine) (MW 1,500-1,800 Da, Cat #: SSP-060) (Gelest, Inc.) and a reaction was allowed to take place while mixing.

After about 2 hours, the glass bead was sufficiently washed with an ethanol solution and filtered under vacuum until dry. Then it was sintered in an oven at 110° C. for 40 minutes. As a result, a glass bead having a surface coated with polyethyleneimine ("PEIM") was obtained. Since the PEIM is capable of non-specifically binding to a cell, the glass bead may be employed for non-specifically separating a cell.

3. Experiments for Extracting a Nucleic Acid

Gram-positive bacteria of *S. aureus* ("SA") were diluted in a sodium acetate buffer (50 mM, pH 4) to a concentration of $10^6$ colony-forming units per milliliter (CFU/ml).

Then, 1 mL of the SA solution was introduced into a bead chamber by flowing through a channel, which is an inlet, to the chamber, at a flow rate of 200 ul/min for 5 minutes. The process was conducted with both the inlet and outlet of the chamber open.

Then, a Tris buffer (Tris, pH 8, 10 mM) for washing the bead chamber was flowed through the channel and the chamber, at a flow rate of 200 microliters per minute (ul/min), and subsequently air was injected for drying the beads.

Lastly, after injecting 0.02 N NaOH solution (6 uL) into the bead chamber at a very low rate, e.g., 30 kilopascal (kPa), the inlet and outlet were closed, and cells were disrupted by vibrating the PDMS membrane at a frequency of 10 Hz with +80 kPa and −80 kPa, by adjusting the Solenoid valve by means of the LabVIEW program. After the cell disruption process, the inlet and outlet were opened, 100 kPa of pressure was applied, 14 ul of NaOH solution was additionally injected by flowing through the chamber, and then the cell disruption product was recovered through the outlet. Thus, a cell disruption product (i.e, lysate) containing nucleic acid in a total of 20 ul of NaOH solution was obtained. For a positive control sample, a benchtop bead beating process was conducted.

As the positive control experiment, 1 ml of SA dilute solution, which was prepared for the subject experiment, was centrifuged at 13200 revolutions per minute (rpm) for 20 minutes to precipitate SA bacteria, and then the supernatant was removed. A volume of 20 μL of 0.02N NaOH, the same cell lysis solution used in the device, and glass beads were put into a container including the precipitated bacteria and mixing was carried out with a vortexer (GENIE 2, Fisher) at maximum speed (Max. 3200 rpm) for 5 minutes, to obtain a cell disruption product.

For a negative control, the supernatant was removed after centrifugation, deionized ("DI") water alone was put into the container including the precipitated bacteria, and mixing was carried out with the above vortexer at the maximum speed for 5 minutes.

4. Real-Time Polymerase Chain Reaction ("PCR")

The amount of DNA extracted from the cell disruption achieved using the embodiment of the device disclosed herein for actuation times up to 20 min was compared with the amount of DNA extracted from the positive control sample by means of PCR (TMC PCR machine, Samsung). An SA 442 region present in *S. aureus* was tested using the following primers (Applied Biosystems, US), probes and composition of the PCR.

TABLE 1

| | Sequence |
|---|---|
| Sa442 forward primer | 5'-GTT GCA TCG GAA ACA TTG TGT T-3' (SEQ. ID. No. 1) |
| Sa442 reverse primer | 5'-ATG ACC AGC TTC GGT ACT ACT AAA GAT-3' (SEQ. ID. No. 2) |
| Sa442 Taqman probe | 5'-TGT ATG TAA AAG CCG TCT TG-3' (SEQ. ID. No. 3) |

| Component | volume (μl) | Final concentration |
|---|---|---|
| 10× Z-Taq buffer | 0.2 | 1× |
| 25 mM dNTP | 0.16 | 2 mM |
| Z-Taq polymerase | 0.02 | 0.5 U |
| 50 mM forward primer | 0.03 | 1 μM |
| 50 mM reverse primer | 0.03 | 1 μM |
| 20 mM probe | 0.03 | 0.4 μM |
| Water | 0.5 | — |
| Disrupted cell solution | 1 | — |

5. Experimental Results

Figure 7:
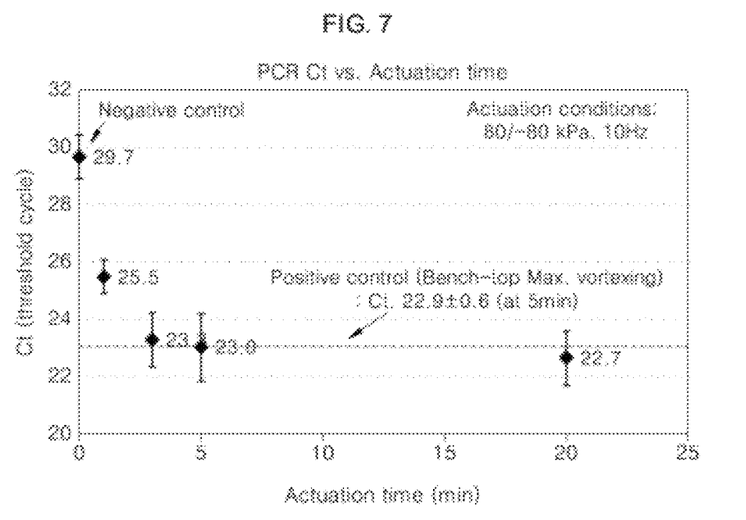
FIG. 7 is a graph showing threshold cycle (number) versus actuation time (minute) representing results of a cell disruption test conducted according to a method of disrupting cells.

The implementation of the cell disruption device and method for five minutes resulted in a similar threshold cycle (Ct) to that obtained in the positive control experiment, as shown in FIG. 7. Based on the experimental results shown in FIG. 7, it may be concluded that an embodiment of the method of disrupting cells according to the invention has similar performance to the performance of the bench top bead beating method, which is well known in the art.

In FIG. 7, the horizontal axis represents the actuation time, i.e., the time taken to disrupt cells in the device, and the longitudinal axis represents Ct.

An embodiment of the micro-device for disrupting cells according to the invention facilitates the disruption of cell membranes or cell walls by beating with microbeads. Therefore, the efficiency of elution of a particular substance in a cell, such as a nucleic acid, substantially increases, while the time for preparation of a sample, such as a nucleic acid preparation for a diagnostic assay, and the cost of the diagnostic assay are substantially reduced. In such an embodiment, the micro-device may be used in various diagnostic tools, such as a PCR apparatus, a microarray apparatus and a sequencing apparatus, for example, thereby increasing the accuracy of the diagnosis performed by the various diagnostic tools. Example 2: Cell lysis effect with respect to liquid volume fraction 1. Manufacture of Cell or Virus Lysis Device A cell or virus lysis device may be manufactured by disposing a commercially available elastic membrane between two glass chips. Chambers or channels may be defined using an entirety of a glass chip or a portion of the glass chips, which may then be combined with the elastic membrane therebetween, thereby completing the manufacture of the cell or virus lysis device.

In the current example, first and second glass chips were manufactured by defining channels and chambers in a glass wafer by photolithography, etching, and wet etching processes, which are well known and the details of which can be determined without undue experimentation. After having been cleaned with a Piranha solution (i.e., a combination of sulfuric acid and hydrogen peroxide), a 6-inch glass wafer (borosilicate, 700 μm thick) was deposited with a 500 nanometer (nm) thick amorphous silicon layer by low-pressure chemical vapor deposition ("LPCVD"). Then, a patterning process was performed on a portion of the deposited silicon layer exposed through a photoresist film. The exposed part of the silicon layer was removed by dry etching. Afterwards, the photoresist film was stripped off, and the exposed glass wafer was wet-etched with a hydrofluoric acid solution (HF, 49%) to form a channel having a depth of about 100 μm and a width of about 200 μm. In the etching process for forming the channel, a weir (protrusion) projecting about 20 μm toward an inner center from an inner surface of the channel was formed to confine beads. The weir was formed to serve both as a valve seat and a bead trapping weir.

Then, after the silicon layer was removed, a dry film resist ("DFR") was coated and patterned. Then, a chamber including beads (ca. about 15.5 μl) and holes for fluid inflow or outflow were formed using a sand-blasting method. Subsequently, the glass wafer was diced into chip-shaped pieces, which were then washed with plasma. A fluidic chip ("first glass chip") including the above-manufactured chamber to contain the beads, and a pneumatic chip ("second glass chip") including a chamber to function as a pneumatic pump and not containing beads were permanently coupled with a 254 μm thick PDMS layer (available from Rogers Corporation) which was activated with a plasma between the first and second glass chips as an intermediate layer. The PDMS layer, which is a monolithic flexible layer, was used to control fluid flow and used as a pump and a valve and as an actuator for inducing collisions between the beads by pneumatic vibration.

About 15-16 milligrams (mg) (about $2 \times 10^5$ in number) surface-modified glass beads were put into the bead chamber, which was then sealed using a PCR-compatible adhesive tape (available from Applied biosystems). The attached tape was covered with a polycarbonate plate to prevent the tape from bending during operation such as a DNA extraction.

Operation of the PDMS layer was controlled by applying a positive pressure or a negative pressure to the pneumatic chamber with a Solenoid valve array (5070-5DC, available from SMC) connected thereto. The valves were coupled to an electropneumatic-regulator (ITV0030-3BL, available from SMC) and LabVIEW software (available from National Instruments). Operation of the valves associated with fluid transfer was visualized through an interface of the LabVIEW software in each step to monitor extraction of nucleic acids.

Figure 8:
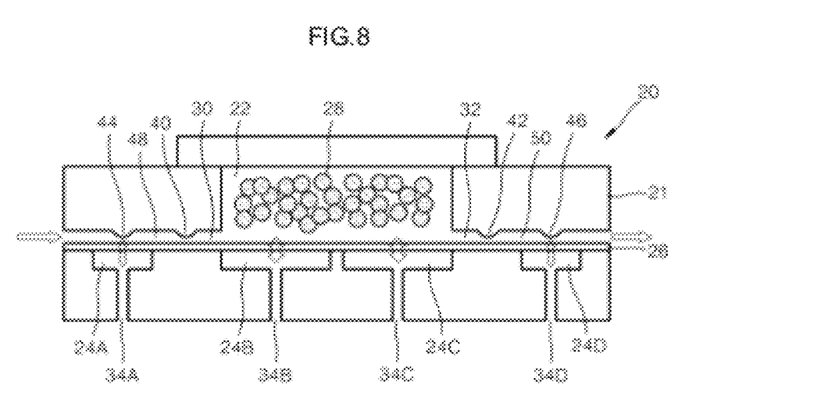
FIGS. 8 and 9 illustrate a cell lysis device according an embodiment of the cell lysis device.

FIGS. 8 and 9 illustrate a cell lysis device used in the current Example. FIG. 8 is a cross-sectional view of the cell lysis device using bead beating in which collisions of beads are induced by the vibration of a PDMS layer. Referring to FIG. 8, an inlet with a first protrusion 40 and an outlet with a second protrusion 42 are connected to an inlet port and an outlet port, respectively, via fluid channels 48 and 50. First and second valve sheets 44 and 46 are formed on an upper plate, which defines the inlet and the outlet to correspond to the inlet and outlet ports, respectively. Pneumatic chambers, specifically first to fourth chambers 24A to 24D, are disposed in a lower plate and the first and the fourth chambers 24A and 24D correspond to the first and second valve sheets 44 and 46, respectively. First to fourth ports 34A to 34D are fluidly connected to the first to fourth chambers 24A to 24D.

Figure 9:
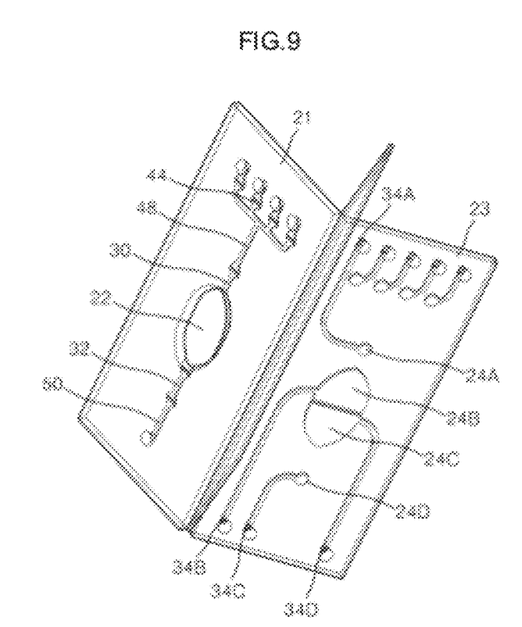

FIG. 9 is an enlarged view of a 3-layered cell lysis device including monolithic glass, PDMS and glass, and fluidic and pneumatic components of the cell lysis device.

2. Glass Bead Modification

After having been washed with a Piranha solution and then with distilled water, glass beads having a diameter of about 30 μm to 50 μm (available from Polysciences, Inc.) were filtered and vacuum-dried.

Afterwards, a 5% (volume/volume) trimethoxysilylpropyl-modified PEI (poly(ethyleneimine)-trimethoxysilylpropyl: PEIM) solution (available from Gelest, Inc.) in ethanol was prepared as a bead-surface modification solution. The beads were put into the bead-surface modification solution and reacted for about 2 hours by gentle mixing, followed by filtration and washing with fresh ethanol three times. The final recovered glass beads were incubated in a 110° C. oven for 50 minutes, to obtain glass beads having surfaces coated with PEIM. PEIM is known to be able to non-specifically bind to cells, and thus the glass beads coated with the PEIM may be used to nonspecifically separate cells.

3. Nucleic Acid Extraction

A 1 mL sodium acetate buffer (50 millimolar (mM), pH 4, available from Sigma-Aldrich) containing $10^6$ colony-forming units per milliliter (CFU/mL) of a sample *S. aureus* or Methicillin-resistant *Staphylococcus aureus* ("MRSA"), a 0.5-mL tris(hydroxymethyl)aminomethane ("Tris")-ethylenediaminetetraacetic acid ("EDTA") ("TE") buffer (10 mM Tris, 1 mM EDTA, pH 8.0, available from Ambion) for washing, and a 10 μl or 20 μl NaOH (0.02 normal (N), available from Sigma-Aldrich) for lysis were stored into a liquid reservoir beforehand. The liquid solution was transferred by a pressure-driven operation. An operating liquid pressure was determined through a preliminary test. Initially, while applying a pressure of 150 kiloPascals (kPa) from above the PDMS layer, the sample solution was directed through the chamber containing the beads at 30 kPa and at about 200 μl/minute. After flowing through the chamber, the solution was recovered to evaluate a cell capture efficiency. After the initial loading of the sample, the washing solution was directed through the chamber containing the beads at about 500 μl/min (80 kPa) to wash it, which was then air-dried at about 100 kPa for about 30 seconds. To lyse the captured cells, 6 μl of the lysis solution (0.02 N NaOH) was injected into the chamber containing the beads, and valves on opposite sides of the chamber were closed. Subsequently, pressures of two pneumatic chambers were adjusted to about 80 kPa and about −80 kPa, respectively, by an adjustment of a Solenoid valve controlled via a Labview program, to vibrate the PDMS layer at a frequency of about 10 Hz for about 5 minutes, thereby performing a cell lysis process. After the cell lysis process, with the inlet and the outlet opened, 4 μl or 14 μl of the NaOH solution was injected with an application of a fluid pressure of about 100 kPa, to recover a lysed cell product through the outlet. The resulting lysed cell product containing a nucleic acid was 10 μl or 20 μl in total. The overall process took about 20 minutes or less. No additional DNA purification was performed.

Experiments with a positive lysis control ("PLC") and a negative lysis control ("NLC") were conducted as follows.

The experiment with a PLC was conducted using two different top bench lysis methods: an enzymatic method and a bead beating method. Two 1 mL sample solutions containing $10_4$ CFU/mL and $10_6$ CFU/mL of *S. aureus* were centrifuged in microcentrifuge tubes at about 13, 200 revolutions per minute (rpm) for about 20 minutes to precipitate cells. Then, the supernatant was removed from each centrifuged product. The precipitated pellets were treated using the two methods. In the enzymatic method, after an incubation of the cell pellets with a lysostaphin solution (200 milligrams per milliliter (mg/mL), available from Sigma) at about 37° C. for about 30 minutes, 20 µl of a purified DNA solution was obtained from the incubated product by using a Qiagen DNA extraction kit (Cat 51304, QIAamp DNA Mini Kit) according to the operation protocols of the kit. In the bead beating method, after an addition of 30 mg of bare glass beads and 20 mL of the lysis solution (0.02 N NaOH solution or distilled water) to the cell pellets, the combination was vigorously vortexed using a vortexer (GENIE 2, available from Fisher Scientific) at a full velocity for about 5 minutes. After simple centrifugation, an extracted DNA solution (a lysed cell product) was recovered. In the experiment with the NLC, after an addition of distilled water alone, the cell pellets were vigorously vortexed with no glass beads present, using a vortexer (GENIE 2, available from Fisher Scientific) at a full velocity of about 3,200 rpm for about 5 minutes. Using the resulting lysed control product, PLC, and NLC as templates, a target nucleotide sequence was amplified. This amplified product was compared with a result of amplifying the target nucleotide sequence with the DNA solution extracted using the bead beating based cell lysis device used as a template. For accurate comparison, a total number of S. aureus cells injected into the chamber and a final volume of the DNA extraction solution in each control group were controlled to be consistent with those of the test sample.

4. Real-Time PCR Amplification

To lyse cells and qualify extracted DNA, real time-PCR was conducted using a GenSpector$^R$ TMC-1000 instrument (available from Samsung Electronics). A primer set (forward: 5'-GTT GCA TCG GAA ACA TTG TGT-3 (SEQ ID No. 1), reverse: 5'-ATG ACC AGC TTC GGT ACT ACT AAA GAT-3' (SEQ ID No. 2), and GeneBank accession number AF033191) specific to the SA442 fragment of the S. aureus genome, and a primer set (forward: 5'-ACG AGT AGA TGC TCA ATA-3' (SEQ ID No. 3), reverse: 5'-GGA ATA ATG ACG CTA TGA T-3' (SEQ ID No. 4), and GeneBank accession number EF190335.1) specific to the mecA fragment of the MRSA genome were designed using a Primer3 software (Whitehead Institute/MT Center for Genome Research).

A PCR reaction mixture (about 2 µl) was prepared to have the following concentration: 0.4 µM of Taqman probe (FAM-5'-TGT ATG TAA AAG CCG TCT TG-3'-MGB-NFQ (SEQ ID No. 5) for S. aureus; and FAM-5'-CCA ATC TAA CTT CCA CAT ACC ATC T-3'-BHQ1 (SEQ ID No. 6) for MRSA), a 1× Z-Tag buffer (available from Takara Bio), 1 micromolar (µM) of each primer (available from Applied Biosystems or Sigma), 0.05 U of Z-Taq polymerase (available from Takara Bio), a 0.2 mM dNTP (available from Takara Bio), 0.5 µl of PCR-grade water (available from Ambion), and 1 µl of an extracted DNA solution. After the PCR reaction mixture was loaded into a PCR chip, thermal cycling was conducted as follows: denaturation at 95° C. for 1 minute and elongation at 60° C. for 4 seconds. The PCR conditions were designed to attain a PCR amplicon size of 72 base pairs (bp) for S. aureus and 98 bp for MRSA. The PCR amplicon sizes were further identified by gel electrophoresis (Agilent 2100 Bioanalyser, available from Agilent Technologies).

5. Experimental Results (1) Experimental Results of Control Sample

Cell lysis and/or DNA purification effects were evaluated using a threshold cycle (Ct). Ct values of PLC samples are shown in Table 1. The Ct values in Table 1 are an average from three repeated experiments on each group.

TABLE 1

| Number of loaded S. aureus cells (CFU) | Benchtop bead beating method | | Enzymatic method (lysostaphin) |
|---|---|---|---|
| | NaOH (0.02 N) | Distilled water | |
| About $10^4$ | 30.5 ± 0.35 | 34.5 ± 0.26 | 31.6 ± 0.56 |
| About $10^6$ | 23.7 ± 0.29 | 26.7 ± 0.15 | 25.7 ± 1.43 |

To improve lysis efficiency, the benchtop bead beating method was performed with a lysis solution containing a surfactant or a chemical substance. In the current example, a NaOH solution (0.02 N), known not to interfere with PCR amplification without additional purification, was used. Bead beating effects with the NaOH solution or distilled water in Table 1 indicate that NaOH, which chemically destructs cell walls, contributes to improving the DNA extraction efficiency. While not wanting to be bound by theory, regarding the enzymatic lysis of S. aureus, lysostaphin was selected because it specifically cleavages cross-linking pentaglycine bridges in the cell wall of staphylococci. The benchtop bead beating method with the NaOH solution shows a performance more than or equivalent to that of the enzyme-based DNA extraction method. Therefore, results with the used cell or virus lysis device were compared with those with the benchtop vortexing machine to evaluate efficiency. Optical density measurement is an approximate quantification of cells, which have caused variations in the Ct value of the PLC even at the same optical density with a standard deviation of about 1.5. The NLC sample vortexed with distilled water alone had a Ct value of about 31.5 at a cell concentration of $10^6$ CFU/mL.

(2) Cell Capture Results

In the present example, basic operations were as follows: (1) capturing cells on glass beads, (2) washing and drying, (3) lysing cells with in-situ bead beating, and (4) eluting the extracted DNA solution. Bacteria cells may be specifically or non-specifically captured on a solid substrate.

In addition to cell specific immunoaffinity techniques, pathogenic bacteria cells may be captured by non-specific cell capture techniques using surface thermodynamics or electrostatic interaction. In the present example, to evaluate the effect of long-range Coulombic electrostatic interactions to non-specific cell capture glass beads were modified to be positively charged on the surface. Surfaces of the glass beads were treated to have positive amine derivatives by reaction with an organosilane compound including poly(ethyleneimine) ("PEI").

After the interior of the microfluidic chamber was filled with the surfacemodified glass beads, 1 mL of a sample solution containing $10^6$ CFU/mL of S. aureus cells was directed through the microfluidic chamber. Initially, results with non-modified glass beads and those with modified glass beads were compared in terms of electrostatic interaction. As a result, a Ct value of the DNA extracted with the modified glass beads was smaller by 2 than that of the DNA extracted with the non-modified glass beads, thereby indicating an increase of about 4 times in cell capture efficiency through the surface modification, considering that a difference in Ct of one (1 Ct) indicates two times the difference in initial template copy number.

To obtain quantitative data of the cell capture capacity of the cell lysis device used in the present example, after flowing through the chamber, the sample solution was recovered, centrifuged, and disrupted using a benchtop vortexing machine together with bare glass beads and an NaOH solution, as used with the PLC (hereinafter, the lysed product is referred to as "AC"). A Ct value of the AC was compared with that of a DNA solution ("AE") eluted from the bead-beating device through appropriate operations. A difference between the two values was used as a measure of cell capture efficiency and capacity of the bead beating device.

When 1 mL of each *S. aureus* sample solution having a different cell concentration of $10^4$, $10^5$, $10^6$, $10^7$, and $10^8$ CFU/mL was loaded, the differences between the AC and AE were maintained at about 5 or greater in the sample solutions of from $10^3$ CFU/mL to $10^7$ CFU/mL, but was reduced to about 2.5 at $10^8$ CFU/mL. Considering that one hundred times the difference in initial template copy number may induce a difference in Ct ($\Delta$Ct) of about 3.3, the capture efficiency was found to be about 90%. The manufactured bead-packed microfluidic device had a capacity of $10^7$ CFU or greater of *S. aureus* cells. After cell capture, the bead-packed microchamber was washed, dried with air, and then filled with the lysis solution. These results indicate that the applied cell capture method is appropriate to disrupt the captured cells by in-situ bead beating, rather than to release the captured cells. Other cell capture methods using, for example immunoaffinity, may be integrated with the cell lysis device used in the present example by employing appropriate solid surface chemistry.

(3) Effects of Liquid Volume Fraction (fL) on Bead Beating Cell Lysis

Figure 10:
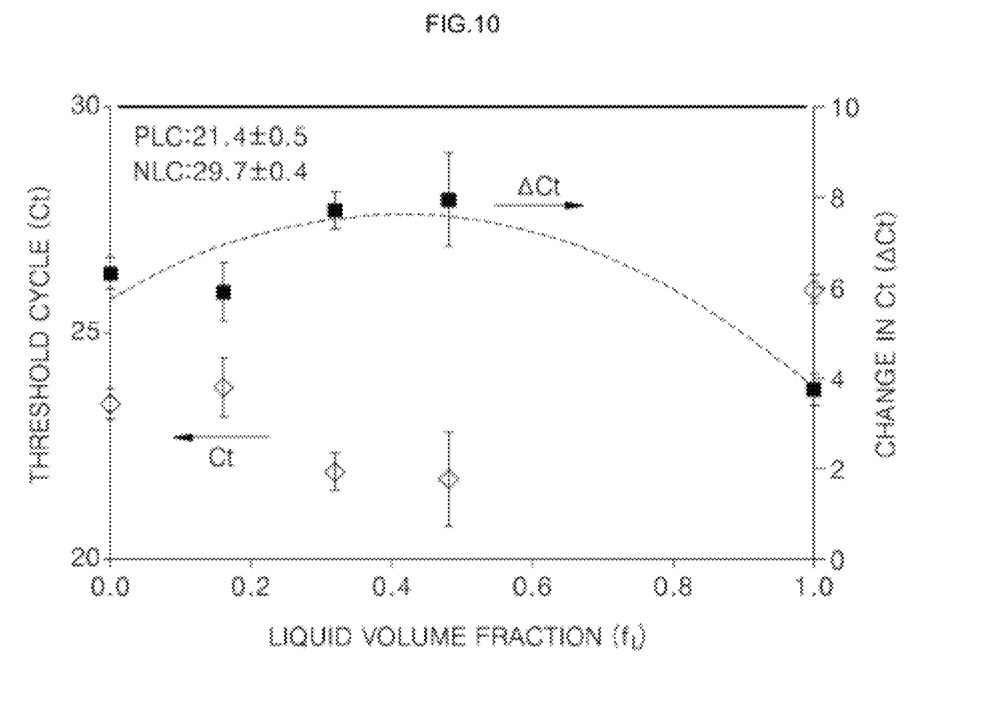
FIG. 10 is a graph of threshold cycle (Ct) and change in Ct (ΔCt) versus liquid volume fraction (fL) showing cell lysis efficiency with respect to changes in liquid volume fraction (fL).

Effects of various factors on bead beating cell lysis were investigated. As a result of experiments at a membrane vibration frequency (from about 5 Hz to about 10 Hz), a membrane operating pressure (from about 20 kPa to about 80 kPa), and a depth of a pneumatic displacement chamber (from about 100 μm to about 200 μm), the factors were found not to be statistically significant on PCR Ct values. Effects of liquid viscosity on bead beating cell lysis were investigated with respect to changes in liquid volume fraction (fL) during bead beating induction, the liquid volume fraction being defined by the volume of the lysis solution with respect to the pure void volume of the microfluidic chamber packed with beads. The final elution volume of DNA was adjusted to be 20 μl, by adding a NaOH solution when the extracted DNA was eluted from the chamber. FIG. 10 is a graph of threshold cycle (Ct) and change in Ct ($\Delta$Ct) versus liquid volume fraction (fL) showing cell lysis efficiency with respect to changes in liquid volume fraction (fL).

Referring to FIG. 10, the liquid volume fraction (fL) is found to correlate with cell lysis efficiency, and, while not wanting to be bound by theory, it is believed that liquid volume fraction (fL) is a determining factor of cell lysis efficiency. The cell lysis efficiency was high at a liquid volume fraction (fL) of 0.6 or less, and in particular, was higher at 0.5 or less, and still higher at between 0.3 and 0.5. Efficient cell lysis was also possible at a liquid volume fraction (fL) of 0. This is attributed to the fact that the viscosity of the liquid solution (NaOH) is 100 times or greater than that of air, and thus, a relative amount of the liquid solution (NaOH) markedly affects the viscosity of the mixed solution (gas and liquid).

It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A method of disrupting one or more cells or viruses, the method comprising:

introducing a sample solution containing the cells or viruses into a first chamber of a micro-device for disrupting one or more cells or viruses, wherein the micro-device comprises:

the first chamber;

a second chamber which can be sequentially pressurized and depressurized;

a flexible and elastic membrane between the first chamber and the second chamber and defining at least a part of the wall of the first chamber and second chamber, wherein the membrane vibrates when the second chamber is sequentially pressurized and depressurized; and a solid support for disrupting cells contained in the first chamber and present as a separate material with respect to the chamber wall;

disrupting the cells or viruses by vibrating the flexible and elastic membrane between the first chamber and the second chamber by flowing a fluid into and out of the second chamber through a port, wherein the disrupting comprises periodically or non-periodically adjusting the pressure of the interior of the second chamber such that the flexible membrane is vibrated; and releasing resultant disrupted cells or viruses from the first chamber of the micro-device;

wherein the micro-device further comprises an upper plate with a space defining the first chamber and a lower plate with a space defining the second chamber; and wherein the flexible membrane is disposed between the upper plate and the lower plate, the first chamber is delimited by the upper plate and the membrane, and the second chamber is delimited by the lower plate and the membrane.

2. The method of claim 1, wherein the introducing the cells or viruses comprises passing a solution containing the cells or viruses at a rate of 100 to 500 ul/min through the first chamber such that the cells or viruses in the solution are retained on the solid support, wherein the first chamber has a volume of 1 ul to 100 ul and the solution has a pH of 3.0 to 6.0 and a salt concentration of 10 mM to 500 mM, and wherein the solid support comprises on its surface a binding material which binds to a cell or a virus.

3. The method of claim 1, further comprising washing the solid support with wash buffer by flowing the wash buffer at a rate of 100 to 500 ul/min through the first chamber to remove impurities form the solid support, wherein the wash buffer has a pH of 3.0 to 6.0 and a salt concentration of 10 mM to 500 mM.

4. The method of claim 3, wherein the solution comprises both animal cells and bacterial cells, and the animal cells are impurities that are selectively removed from the solid support while retaining the bacterial cells.

5. The method of claim 1 further comprising, prior to the step of introducing the sample into the first chamber, diluting the sample with a phosphate buffer or an acetate buffer having a pH of 3.0 to 6.0 and salt concentration of 10 mM to 500 mM to obtain a solution containing cells or viruses having a pH of 3.0 to 6.0 and salt concentration of 10 mM to 500 mM.

6. The method of claim 1, further comprising providing a cell lysis solution to the first chamber prior to or during the step of disrupting.

7. The method of claim 6, wherein the cell lysis solution comprises at least one of NaOH, KOH, chaotrope, a surfactant, a cell wall degrading enzyme and a biological buffer.

8. The method of claim 1, wherein disrupting the cells comprises moving the plurality of solid supports by vibrating the flexible and elastic membrane.

9. The method of claim 1, wherein disrupting the cells or viruses comprises periodically or non-periodically adjusting the pressure of the interior of the second chamber such that the flexible and elastic membrane is vibrated.

10. The method of claim 9, wherein the cell lysis solution is NaOH solution or KOH solution, and the method further comprises performing PCR using the lysed product obtained from the disrupting step as a template without any further purification step.

11. The method of claim 1, wherein the solid support comprises a microparticle.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Sa442 Forward Primer

<400> SEQUENCE: 1
gttgcatcgg aaacattgtg tt                                              22

<210> SEQ ID NO 2
<211> LENGTH: 27
<212> TYPE: DNA
<213> ORGANISM: Artificial Sequence
<220> FEATURE:
<223> OTHER INFORMATION: Sa442 Reverse Primer

<400> SEQUENCE: 2
atgaccagct tcggtactac taaagat                                         27

<210> SEQ ID NO 3
<211> LENGTH: 20
<212> TYPE: DNA
<213> ORGANISM: Artificial Sequence
<220> FEATURE:
<223> OTHER INFORMATION: Sa442 Taqman Probe

<400> SEQUENCE: 3
tgtatgtaaa agccgtcttg                                                 20
```